United States Patent [19]

Guesdon et al.

[11] Patent Number: 4,668,637

[45] Date of Patent: May 26, 1987

[54] METHOD FOR DETECTING AND DOSING BY ERYTHROADSORPTION A BIOLOGICAL SUBSTANCE

[75] Inventors: Jean-Luc Guesdon, Paris; Stratis Avrameas, La Celle St-Cloud, both of France

[73] Assignee: Institut Pasteur, France

[21] Appl. No.: 619,467

[22] PCT Filed: Sep. 30, 1983

[86] PCT No.: PCT/FR83/00198

§ 371 Date: May 30, 1984

§ 102(e) Date: May 30, 1984

[87] PCT Pub. No.: WO 84/01436

PCT Pub. Date: Apr. 12, 1984

[30] Foreign Application Priority Data

Oct. 1, 1982 [FR] France ................. 82 16565

[51] Int. Cl.[4] ................. G01N 33/567; G01N 33/543; G01N 33/555; G01N 33/556
[52] U.S. Cl. ................. 436/504; 436/518; 436/520; 436/521; 436/528
[58] Field of Search ............... 436/504, 520, 521, 518, 436/528

[56] References Cited

U.S. PATENT DOCUMENTS

| 3,708,572 | 1/1973 | Pegtom et al. | 436/521 |
| 3,987,159 | 10/1976 | Spona et al. | 436/521 |
| 4,371,515 | 2/1983 | Chu | 436/548 |
| 4,493,793 | 1/1985 | Chu | 436/528 |
| 4,526,871 | 7/1985 | Avrameas et al. | 436/504 |

FOREIGN PATENT DOCUMENTS

| 0041426 | 5/1981 | European Pat. Off. |
| 2476320 | 2/1980 | France |
| 8102790 | 10/1981 | World Int. Prop. O. |
| 8200203 | 1/1982 | World Int. Prop. O. |

OTHER PUBLICATIONS

Pereira, J. Immunol. Methods, 63(1983) 25-34.
Lawny et al., Chemical Abstracts, 90(1979) #70358e.

Primary Examiner—Christine M. Nucker
Attorney, Agent, or Firm—Jones, Tullar & Cooper

[57] ABSTRACT

A process for the detection of a biological substance immobilized on a support including
(1) incubating, after washing, the substance immobilized on a support with the product of coupling of a specific ligand with a ligand capable of reacting with erythrocytes;
(2) adding erythrocytes;
(3) immersing the whole in a solution of a fixing agent and
(4) measuring the erythroadsorption, after having turned the support over in order to permit the removal of the red cells which have not reacted.

12 Claims, 1 Drawing Figure

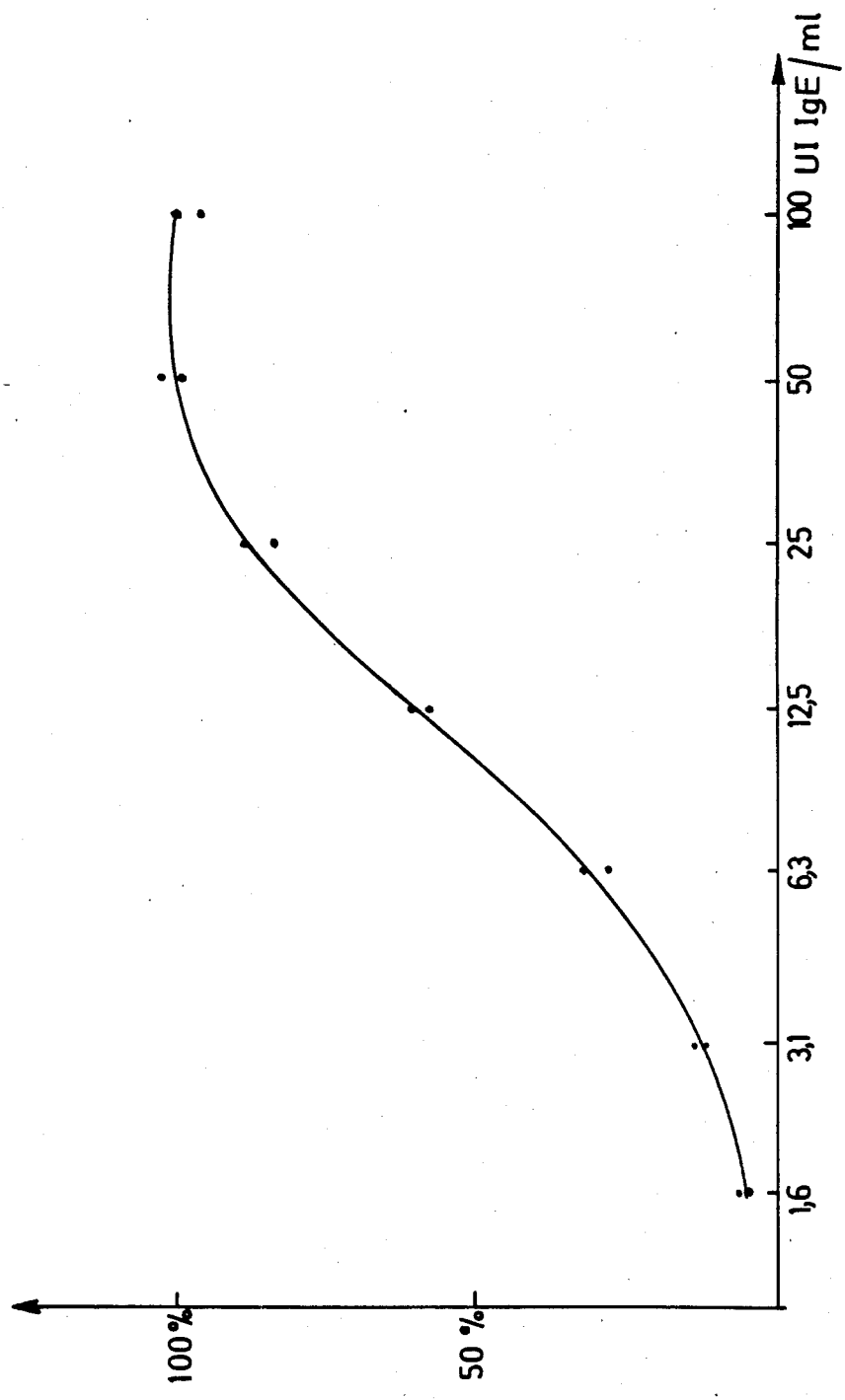

METHOD FOR DETECTING AND DOSING BY ERYTHROADSORPTION A BIOLOGICAL SUBSTANCE

The present invention relates to the field of biology and more particularly to the detection, by erythroadsorption, of a biological substance immobilised on a support.

It relates in particular to improvements to the process for detection and determination of a biological substance by erythroadsorption described in patent application FR No. 80/15,293.

In this patent application FR No. 80/15,293 a process for detecting and determining a biological substance by erythroadsorption has already been described. This process employs, as a reagent for determination, the product of coupling a specific ligand with a ligand capable of reacting with erythrocytes, and erythrocytes as a developer.

This process for detection and determination of a biological substance by erythroadsorption consists in:

(1) immobilising on a support a substance having a fixing affinity for the biological substance to be determined;

(2) incubating this substance with the liquid medium containing the biological substance to be determined;

(3) incubating, after washing, the resulting reaction medium with the product of coupling of a specific igand with a ligand capable of reacting with erythrocytes.

(4) Adding erythrocytes; and (5) Determining the erythrocyte adsorption.

This process is suitable for determining, as biological substances, antigens, antibodies, haptens, hormones immunoglobulins and other substances of biological interest.

According to the teaching of this Patent FR No.80 15,293, the determination of erythroadsorption can be carried out in several ways.

For example, it is possible to establish visually that the red cells are adsorbed at the surface of the support on which the substance having a fixing affinity for the biological substance to be determined has been immobilised. In this case, the process makes it possible to identify a particular biological substance in a given biological liquid. If, on the other hand, the biological liquid does not contain the particular biological substance, the erythrocytes are not adsorbed and form a residue at the bottom of the receptacle, for example wells of the microplate. The process for determination by erythroadsorption according to this Patent FR No. 80/15,293 also makes it possible to determine a given biological substance quantitatively. For this purpose, the red cells which have not reacted are removed, for example by suction with a pipette. The adsorbed erythrocytes are then lysed, for example with distilled water, and the substances liberated by the red cells, for example haemoglobin or the substances introduced artificially by the experimenter, are then determined by spectrophotometry.

Haemoglobin can also be determined by an enzymatic reaction. It is possible, for example, to employ one of the peroxidase substrates, such as ortho-dianisidine, or ortho-phenylenediamine. The reading is also carried out by spectrophotometry, at 400 nm for orthodianisidine and 492 nm for ortho-phenylenediamine.

The quantity of substances liberated by the red cells, for example the quantity of liberated haemoglobin, is proportional to the quantity of the substance to be determined, which makes it possible to obtain, for example, the estimate of an antigen or an antibody present in the sample by referring to a standard range of haemolysis of red cells produced under the same conditions.

The quantitative determination of erythroadsorption as defined above therefore requires the removal of red cells which have not reacted and the determination of the substances liberated by the red cells or substances introduced artificially by the experimenter.

In this process, the biological substance to be determined is immobilised on a support by specific fixation, that is to say through the intermediacy of a substance having a fixing affinity for the biological substance to be determined.

It is also possible to determine by erythroadsorption, using the same operating procedure, substances which are fixed on a support by any other means, for example by passive adsorption or by chemical bonding.

It has now been found that the determination of erythroadsorption can be carried out without involving a step for determination of substances liberated by the red cells which have been adsorbed or substances introduced by the experimenter. This determination is carried out in a simpler manner and permits a better quantification than that described in Patent FR No. 80/15,293.

Accordingly, the present invention relates to a process for the detection and/or determination, by erythroadsorption, of a biological substance immobilised on a support, which consists in determining the erythroadsorption after having, on the one hand, removed the red cells which have not reacted and, on the other hand, fixed the adsorbed red cells chemically on the immuno adsorbent, solely by the use of a solution of a fixing agent.

In its most general form, the process of the invention consists in:

(1) incubating, after washing, the substance immobilised on a support with the product of coupling of a specific ligand with a ligand capable of reacting with erythrocytes;

(2) adding erythrocytes;

(3) immersing the whole in a solution of a fixing agent, (4) measuring the erythroadsorption, after having turned the support over in order to permit the removal of the red cells which have not reacted.

Using the solution of fixing agent employed in the process of the invention, the erythrocytes adsorbed at the surface of the support on which the biological substance to be detected has been immobilised are fixed chemically and rapid elimination of erythrocytes which have not reacted is possible. In this way, a homogeneous layer of adsorbed and chemically fixed erythrocytes, the density of which is a function of the concentration of the substance to be detected, is formed on the support.

A "fixing agent" according to the invention is used to designate any agent capable of fixing the erythrocytes on the support while avoiding their haemolysis.

Fixing of living cells is often carried out in histology to enable them to be studied. The fixing agents employed for this purpose must be such that they permit the fixing of the said cells with a minimum of disturbance of the cell structures (see Histochemistry, PEARSE Churchill Livingstone, 3rd ed. 1968 and "La Cellule" (The Cell) M. DURAND and B. FAVARD, Collection Hermann, Paris 1967).

In the present case, it is immaterial whether or not disturbance of the cell structures occurs, but it is absolutely essential that the fixing, when it takes place, is carried out under conditions which avoid the haemolysis of the erythrocytes.

The majority of monofunctional or multifunctional fixing agents employed currently in the field of histology are suitable for the purpose of the invention, in particular aldehydes, such as formaldehyde or glutaraldehyde, the latter being preferred.

The concentration of the fixing agent in the solution must be sufficient to permit the chemical fixing of the erythrocytes which have reacted, but it must not reach the concentration which would cause a massive fixation of all the erythrocytes.

For example, it may be indicated that, when the fixing agent is glutaraldehyde, the concentration of the solution should be between 0.1 and 0.5% by weight.

The coupling product employed as reactant in the process according to the invention is the product of coupling of a specific ligand with a ligand capable of reacting with erythrocytes.

In the present description, "specific ligand" designates any soluble substance which can react specifically with the substance having an affinity for the biological substance to be determined or with the biological substance itself.

In the present description, "soluble substance" designates any substance soluble in the media employed currently for the biological reactions. Aqueous media may be involved, such as the physiological media, or mixtures of aqueous and organic media.

Furthermore, the specific ligand employed must be such that the product of coupling of the specific ligand with the ligand capable of reacting with erythrocytes should be soluble in an aqueous medium.

According to the invention, "aqueous medium" designates the aqueous media, buffered or not, currently employed in the field of biology, such as the phosphate buffer solutions, buffer solutions containing a detergent, such as Tween or gelatine, bovine serum albumin, bovine lactalbumin and other substances normally employed in such fields.

The specific ligands corresponding to such a definition are particularly antibodies, macromolecular antigens, haptens, hormones and their receptors and similar substances. Among the specific ligands mentioned above, those most widely employed are the antibodies and antigens.

The ligand capable of reacting with erythrocytes is a substance which contains sites for recognition of specific determinants of the erythrocytes or substances fixed on erythrocytes.

It is possible to mention, as such ligands, the anti-red cell antibodies, avidin, biotin and similar products. It is also possible to use a lectin. Thus, the product of coupling of a specific ligand with a ligand capable of reacting with erythrocytes can be the product of coupling between a lectin and a specific ligand, such as described in Patent FR No. 80/11,470, cited as a reference. The product of coupling of a specific ligand with a ligand capable of reacting with erythrocytes can also be the product of coupling between an albumin and a specific ligand, such as described in Patent Application FR No. 82/04,247, cited as a reference.

The determination of the erythroadsorption can be carried out either visually, or with a photometer set at 414 nm, a binocular magnifier or an inverted microscope.

The process of the invention is suitable for detecting, either quantitatively or qualitatively, any substance immobilised in any way on a support.

The support employed may be any insoluble flat support, which may or may not incorporate cavities, such as for example sheets or strips, microplates or tubes.

The constituent substance used to make such supports may be cellulose and its derivatives, polyacrylamide, the alkyl polymethacrylates and other polymers of natural or synthetic origin, and glass.

Microplates are advantageously employed to immobilise the biological substance to be determined, for example microplates made of polystyrene, having U-shaped or V-shaped wells or flat-bottomed wells. It is also possible to employ individual tubes and flat supports, for example sheets of cellulose nitrate.

For example, when the support is a sheet of cellulose nitrate, the substance to be detected can be fixed or deposited on it directly or indirectly, for example by impression after an electrophoresis. In this way, human IgG can be detected.

The process of the invention is also suitable for the detection of the clones of hybridomas which synthesize antibodies specific for the antigens which have served to produce the said hybridomas. In this case, the clone supernatants are removed, the supernatants are fixed on cellulose nitrate in the form of a sheet and the presence of the antibody is revealed by adding a specific antigen labelled with a ligand capable of reacting with the erythrocytes.

According to the process of the invention, it is possible to detect an isolated substance as well as a substance present in an impure medium, given that a specific reagent for the substance to be determined is employed.

According to another variant of the process of the invention, the biological substance to be detected can be immobilised on the support in a specific manner, that is to say through the intermediacy of a substance having a fixing affinity for the biological substance in question.

In this particular case, a substance having a fixing affinity for the biological substance to be determined is first immobilised on the support, then this substance immobilised in this way is incubated with the liquid medium containing the biological substance to be determined; it is then possible to carry out a quantitative determination or a determination. In this form, the process of the invention relates to an improvement to the process of detection and determination by erythroadsorption of a biological substance described in Patent Application FR No. 80/15,293.

According to this variant, the process of the invention consists in:

(1) immobilising on a support a substance having a fixing affinity for the biological substance to be estimated;

(2) incubating this substance with the liquid medium containing the biological substance to be determined:

(3) incubating, after washing, the resulting reaction medium with the product of coupling of a specific ligand with a ligand capable of reacting with erythrocytes;

(4) adding erythrocytes;

(5) immersing the whole in a solution of a fixing agent, and (6) measuring the erythroadsorption, after having turned the support over in order to permit the removal of the red cells which have not reacted.

The substance having a fixing affinity towards the biological substance to be determined can be any substance capable of being fixed in a specific manner with the said biological substance. For example, if the biological substance to be determined is an antibody, the substance having a fixing affinity will then be an antigen and vice versa.

The substance having a fixing affinity for the biological substance to be determined is immobilised on any support by the use of conventional techniques.

The supports, for example those consisting of sheets of cellulose nitrate on which the substance having a fixing affinity for the biological substance to be determined is fixed, form a means of making use of the process of the invention.

The first stages of the above process, namely stages 1 to 3, are carried out in accordance with Patent FR No. 80/15,293. If need be, those skilled in the art can refer to the description of this patent.

Nevertheless, the general procedure for determining antibodies will be recalled below, without, however, limiting the scope of the invention to this type of determination alone.

During the first stage of the process of the invention, antigens (Ag) are immobilised on a support.

The immobilisation of the antigens, which in this particular case form the substance having an affinity for the biological substance to be determined, namely the antibody, is carried out for example by passive adsorption or, if necessary, by covalent bonding, depending on the nature of the support.

Stage (2) consists of an incubation of the immobilised antigen with the biological liquid containing the antibody (Ac) to be determined, for example the serum to be titrated. After this incubation stage, during which the antigen (Ag) interacts with the corresponding antibody (Ac), if it is present in the serum to be tested, the support is washed with a buffer solution, for example a solution of a phosphate buffer, if necessary containing a detergent such as "Tween" referred to below as PBS or PBS-Tween.

Stage (3) of the process of the invention consists in incubating the resulting support from stage (2) with a product of coupling of a specific ligand with a ligand capable of reacting with erythrocytes. In this particular case, the specific ligand is an antibody directed against the immunoglobulins of the human or animal species in the serum to be titrated. After this incubation, the resulting system is washed as described above to remove the product of coupling which has not reacted. Next, erythrocytes are added, which are adsorbed by the product of coupling only if the serum to be titrated contains the antibody corresponding to the immobilised antigen, otherwise the erythrocytes are not fixed and fall to the bottom of the receptacle.

According to a preferred embodiment of the process of the invention, whatever the manner of immobilising the biological substance to be determined, sufficient erythrocytes are added to fill to overflowing the wells of the microplate employed as a support, in order to avoid the formation of air bubbles in the wells of the said plate. The said plate is then covered, for example with a flexible film of a plastic. Thus covered, the microplate is immersed in the solution of a fixing agent, for example a solution of glutaraldehyde, and is then turned upside down. The plate floats to the surface of the solution and the film is withdrawn. By proceeding in this manner, the red cells which are not specifically adsorbed are removed from the plate, because they fall to the bottom of the receptacle containing the solution of the fixing agent.

The action of the fixing agent, such as glutaraldehyde, has two effects:

(1) the red cells treated with glutaraldehyde settle more quickly than the untreated red cells;

(2) the red cells bound in a specific manner to the solid phase are then fixed chemically by glutaraldehyde, with the result that the stability is increased.

When the unbound red cells are removed, the plate is turned over, care being taken to avoid the entry of air bubbles into the wells. The wells which received a negative sample are empty. The bottoms of the wells which received the positive sample are covered with a layer of red cells the density of which is a function of the concentration of the substance to be determined.

The final result can be read with the naked eye, with a photometer set at 414 nm or by means of a binocular magnifier or an inverted microscope.

When a flat support is employed for immobilising the biological substance to be detected, for example a sheet, it is fixed in the bottom of a receptacle before the addition of erythrocytes and the procedure is as above.

In order to make use of the process of the invention, use is made of a suspension of erythrocytes the concentration of which is not of critical importance. In practice it is sufficient to choose a concentration capable of providing optimum erythroadsorption. By virtue of the operation of turning the support over, which forms an essential feature of the process of the invention, any excess erythrocytes which may be present do not interfere with the reading to the slightest degree, since they are removed. In general, concentrations of the order of 0.5% are suitable. It is possible, however, without disadvantage, to employ concentrations of 1 or 2%. It will be noted that below 0.5% there is no certainty that the erythroadsorption is at optimum. This represents a considerable advantage, because there is no need to standardise accurately the value of the concentrations of erythrocyte suspensions.

The process of the invention makes it possible to extend the use of the erythroadsorption technique to immuno-chemical methods which require the use of a visualising process. Thus, the processes of autoradiography, of enzymatic colouring, and of fluorescence can advantageously be replaced by this new process which consists in visualising a substance by using in succession a conjugate produced by coupling the specific ligand of the sought substance with a lectin or an anti-red cell antibody, and a suspension of red cells.

The present invention also relates to a kit for the detection of a biological substance, the said kit comprising:

anti-biological substance antibodies to be determined, coupled to a ligand capable of reacting with erythrocytes;
PBS buffer;
a solution of a fixing agent;
a support; and
a reference support.

The reference support employed in the kit according to the invention is obtained by the detection process of the invention. To produce this reference support, a given biological substance is immobilised with the product of coupling of a specific ligand and of a ligand capable of reacting with erythrocytes, erythrocytes which are preferably fresh are then added and the whole is immersed in a solution of a fixing agent, the support is turned over to permit the removal of red cells which have not reacted and a reference support is thus obtained, that is to say a support on which erythrocytes are fixed in a quantity corresponding to the given biological substance.

To illustrate the improvement according to the invention, but without restricting it in any way, the following examples are given:

EXAMPLE 1

Qualitative Detection of Human IgG Adsorbed on a Sheet of Cellulose Nitrate

Two $\mu$l of a 0.1 M borate buffer, pH 8.0, containing various concentrations of human IgG (from 100 $\mu$g/ml to 1 $\mu$g/ml) were deposited on a sheet of cellulose nitrate. After evaporation (15 minutes at room temperature) and saturation with gelatin, the sheet of cellulose nitrate was incubated with a conjugate produced by coupling anti-human IgG antibodies with anti-red cell antibodies. 2 hours later the sheet was washed and attached physically to the bottom of a receptacle. The receptacle was then filled with a suspension (0.5%) of sheep red cells. After 1 hour the red cells were removed by gently turning the receptacle over in a buffered physiological solution containing 0.2% of glutaraldehyde. When all the red cells were removed the sheet was turned over. In this way, it was possible to see a deposit of red cells when the quantity of human IgG fixed on the cellulose nitrate sheet was equal to or greater than 2 ng.

EXAMPLE 2

Determination of Human IgE

By virtue of this process for removal of erythrocytes which have not reacted it is possible to establish standardisation curves by employing given quantities of antibodies and antigens, such as those shown in the attached figure, in which the abscissae show the concentration of IgE in IU/ml of known solutions of IgE and the ordinates the percentage of erythroadsorption relative to the 100% plateau defined for an IgE concentration of 100 IU/ml.

The following procedure was followed to establish this curve: the wells of a flat-bottomed plate were filled with 100 $\mu$l of anti-IgE antibodies (1 g/ml). The plate was incubated for 2 hours at 37° C. and one night at 4° C., then washed with PBS containing 0.1% of Tween 20. The wells then received 100 $\mu$l of a reference serum dilution containing a known quantity of IgE. The plate was then incubated for 4 hours at 37° C. and 1 night at 4° C. After the incubation the plate was again washed and each well received 100 $\mu$l of a solution of anti-IgE antibodies coupled with anti-sheep red cell antibodies. After the incubation (2 hours at 37° C.) and washing of the plate, the wells were filled with 400 $\mu$l of a suspension of sheep red cells (0.5%). An hour later the red cells not adsorbed in a specific manner were removed according to the procedure described in Example 1 and the absorption of the light at 414 nm was measured with a Titertek Multiskan MC photometer. The wells which received the IgE solution at a concentration of 100 IU/ml served as reference (100% of erythroadsorption) to calculate the percentage of erythroadsorption.

EXAMPLE 3

Using a strip of cellulose nitrate prepared according to the process described in Example 1 it is possible to determine the IgG which are present in a sample of serum. The intensity of the stains of erythrocytes which have reacted with the anti-IgG-lectin antibodies is compared to those present on the reference strip and permits the detection and the determination of the IgG which are present in the said sample.

We claim:

1. In a process for the qualitative and quantitative determination of biological substance, comprising the steps of:
   immobilizing the biological substance to be qualitatively and quantitatively determined on a support;
   coupling a specific ligand with a ligand capable of reacting the erythrocytes and forming a product;
   incubating the substance immobilized on the support with the product of the coupling; and
   adding erythrocytes of the incubating substance, wherein the improvement comprises the steps of:
   placing the incubating substance with the erythrocytes in contact with a solution of a fixing agent while separating the erythrocytes not fixed on the ligand, and
   measuring the erythroadsorption as a function of the fixed erythrocytes.

2. In the process as defined in claim 1, wherein the solution of the fixing agent comprises a buffered solution of glutaraldehyde at a concentration of approximately 0.1 to 0.5% by weight.

3. In the process as defined in claim 1, wherein the improvement further comprises the step of:
   turning the support over in the solution with the fixing agent for the separation of the erythrocytes not fixed to the ligand.

4. In the process as defined in claim 3, wherein the solution of the fixing agent comprises a buffered solution of glutaraldehyde at a concentration of approximately 0.1 to 0.5% by weight.

5. In the process as defined in claim 1, wherein the support is provided as flat support.

6. In the process as defined in claim 5, wherein the flat support is provided of cellulose nitrate.

7. In the process as defined in claim 5, wherein the improvement further comprises the steps of:
   providing a receptacle;
   fixing the support within the receptacle; and
   saturating the receptacle with erythrocytes.

8. In the process as defined in claim 1, wherein the support is provided as a microplate having wells.

9. In the process as defined in claim 8, wherein the improvement further comprises the steps of:
   filling the wells to overflowing with erythrocytes.
   covering the microplate with a flexible plastic film;
   immersing the covered microplate in a solution of the fixing agent;
   turning the microplate over in the solution and removing the plastic film; and
   allowing the erythrocytes that are not fixed to the ligand to settle before measuring the erythroadsorption.

10. In a process for the qualitative determination of a biological substance by erythroadsorption, comprising the steps of:

immobilizing a substance having a fixing affinity for the biological substance to be determined on a support;

placing the biological substancce to be determined in a ligand medium;

incubating the immobilized substance with the liquid medium containing the biological substance to be determined to form a reaction medium;

coupling a specific ligand with a ligand capable of reacting with erythrocytes and forming a product;

incubating, after washing, the resultant reaction medium with the product of the coupling; and adding erythrocytes to the incubation of the resultant reaction medium with the product of the coupling, wherein the specific erythroadsorption is determined by the improvement comprising the steps of:

placing the incubation of the resultant reaction medium with the product of the coupling and the added erythrocytes in contact with a solutIon of a fixing agent while separating the erythrocytes not fixed on a ligand; and determining the specific erythroadsorption by haemolysis or counting.

11. In the process as defined in claim 10, wherein the solution of the fixing agent comprises a buffered solution of glutaraldehyde at a concentration of approximately 0.1 to 0.5% by weight.

12. A kit for use in the qualitative and quantitative determination of a biological substance, comprising:

means containing anti-biological substance antibodies to be determined coupled to a ligand capable of reaction with erythrocytes;

means containing a phosphate buffer;

means containing a solution of a fixing agent intended for the treatment of erythrocytes;

a support; and a reference support.

* * * * *